United States Patent [19]

Gambini et al.

[11] Patent Number: 4,645,933

[45] Date of Patent: Feb. 24, 1987

[54] EMISSIVE COMPUTED TOMOGRAPHY

[75] Inventors: Michael R. Gambini, Wallingford; Ronald J. Martone, Cheshire; Donald S. Kearns, Farmington; Gary W. Enos, Guilford, all of Conn.; Rudi Franke; Herbert Schoeppy, both of Espelkamp, Fed. Rep. of Germany

[73] Assignee: Picker International, Inc., Highland Heights, Ohio

[21] Appl. No.: 522,309

[22] PCT Filed: Jun. 16, 1982

[86] PCT No.: PCT/US8200813

§ 371 Date: Jul. 29, 1983

§ 102(e) Date: Jul. 29, 1983

[51] Int. Cl.⁴ .................. G01T 1/164; G01T 1/166
[52] U.S. Cl. ................................. 250/363 S
[58] Field of Search .............. 250/363 S, 363 R; 378/189, 190, 196, 197

[56] References Cited

U.S. PATENT DOCUMENTS

| | | | |
|---|---|---|---|
| 2,967,939 | 1/1961 | Caha et al. | 250/361 R |
| 3,803,417 | 4/1974 | Kok | 378/197 |
| 3,970,852 | 7/1976 | Richey et al. | 250/363 S |
| 3,976,885 | 8/1976 | Brunnett et al. | 250/363 S |
| 4,057,726 | 11/1977 | Jaszczak | 250/363 S |
| 4,064,441 | 12/1977 | Casale | 250/363 S |
| 4,091,492 | 5/1978 | Thomson et al. | 15/21 R |
| 4,216,381 | 8/1980 | Lange | 250/363 S |
| 4,220,861 | 9/1980 | Columbo et al. | 250/363 S |
| 4,223,222 | 9/1980 | Gray et al. | 250/363 S |
| 4,235,454 | 11/1980 | Gray et al. | 250/363 S |
| 4,335,315 | 6/1982 | Waerve et al. | 378/197 |
| 4,445,035 | 4/1984 | Ueyama | 250/363 S |
| 4,459,485 | 7/1984 | Span | 250/363 S |
| 4,503,331 | 3/1985 | Kovacs, Jr. et al. | 250/363 S |

*Primary Examiner*—Alfred E. Smith
*Assistant Examiner*—Carolyn E. Fields
*Attorney, Agent, or Firm*—Watts, Hoffmann, Fisher & Heinke Co.

[57] ABSTRACT

A medical diagnostic system utilizing the principles of nuclear medicine is disclosed. The system includes a gantry having a detector support section supported by a carriage section located on a rail system for movement along a linear path. A nuclear detector is supported on a pair of weighted arms pivotally mounted on the detector support system about an axis perpendicular to the rail system. The detector is itself pivotally mounted near an end of the weighted arm pair for tilting rotation about an axis parallel to the arm pivot axis. Mechanism is provided for rotating the weighted arms additionally about an axis parallel to the rail system, in order to accomplish orbital motion of the detector. All three of these rotational movements are power actuated. A stationary pedestal and cantilevered patient support table is located between the rails of the rail system, with the patient table extending longitudinally with respect to the rails. The upper, or detector supporting section, of the gantry is additionally provided with a degree of freedom wherein it may be rotated about a vertical axis extending through the middle portion of the carriage system, thus disposing the detector for operation at a location alongside, and not between the rails.

11 Claims, 15 Drawing Figures

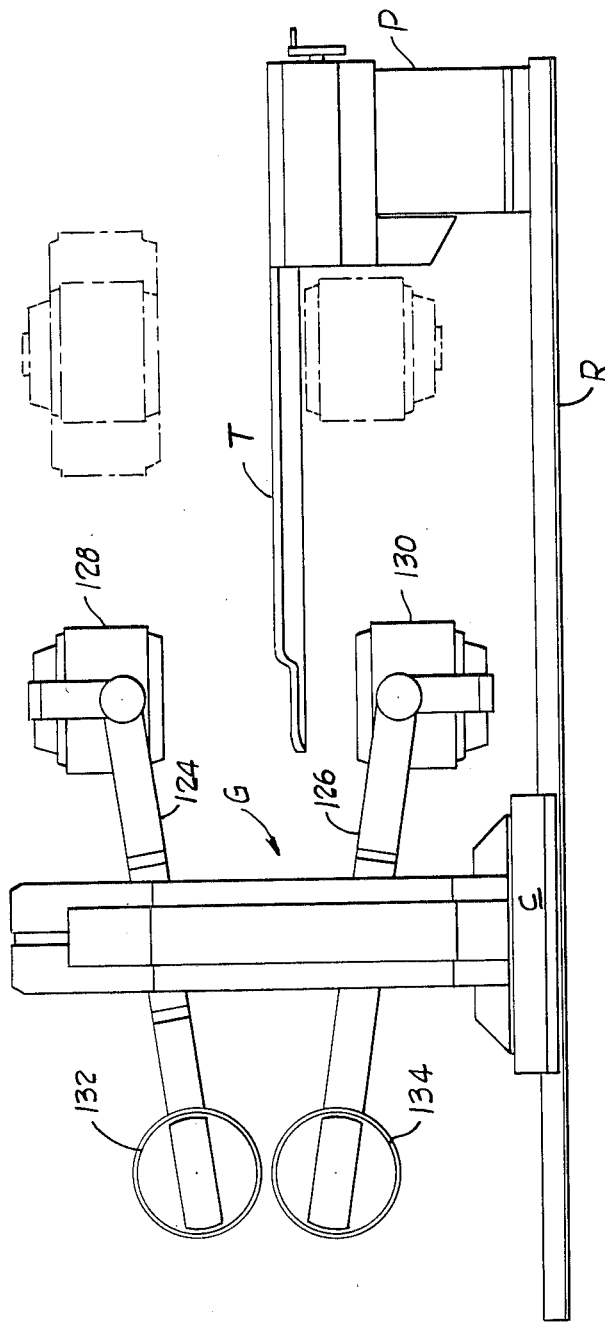
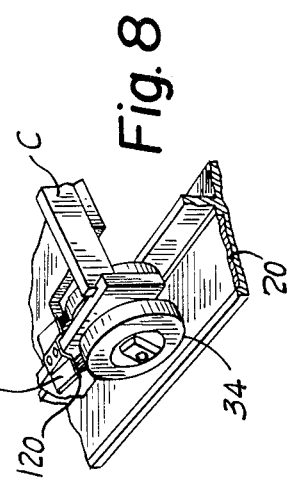
Fig. 8
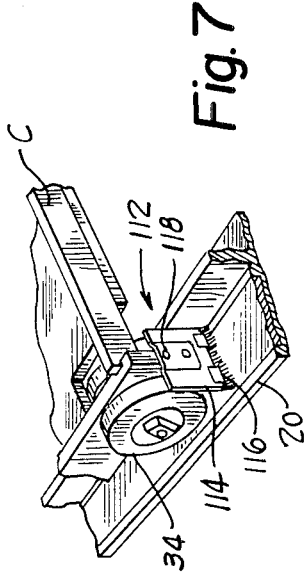
Fig. 7
Fig. 6

EMISSIVE COMPUTED TOMOGRAPHY

TECHNICAL FIELD

This invention relates to nuclear medical imaging and more particularly to a novel and improved mechanism for supporting and manipulating at least one nuclear camera detector for conducting a variety of studies.

BACKGROUND ART

When gamma cameras of the Anger type were first placed in use as medical diagnostic tools, they were used to produce images of organs such as the brain and the thyroid gland. After significant improvements had been made in the cameras and new radioactive isotopes were developed, the cameras commenced to be used for conducting so-called whole body studies for such purposes as detecting cancer of the bone marrow.

Emission computed tomography (ECT) is now used clinically to reconstruct images in a manner which can be likened to its more famous x-ray counterpart, computed tomography, or CT. At least from the standpoint of achieving status as a routine examination procedure, ECT is a more recent development than are whole body studies but utilization of the procedure is increasing.

With an ECT study a nuclear camera detector is orbited about the patient. At each selected point in the orbit, output signals are developed by the detector and its decoding electronics in a conventional manner. The output signals are fed to a computer and after data from a sufficient number of angles or points have been collected, the computer supplies information, typically to an oscilloscope, where an image of a transverse slice through the patient is displayed.

In one commercial system a stand is provided which has a through hole of sufficient size to permit a cantilever supported patient stretcher and a supine patient to pass at least part way through it. The stand assembly carries a rotatable ring which surrounds the hole. A generally rectangular yoke is pivotably supported on the ring for tilting motion about an axis which is perpendicular to and intersects the ring axis. A camera detector is pivotally mounted near one end of the yoke for pivotal adjustment motion about an axis paralleling the yoke tilt axis. A detector counterweight is fixed to the yoke near its end opposite the detector When the described arrangement is in use, a patient is positioned on a cantilever supported and movable stretcher. The yoke is pivoted to position the detector a desired distance from the patient and then fixed in its adjusted position. The detector is moved about its pivot to bring its face into a plane paralleling the through hole axis which is also the axis of orbital rotation for ECT studies. The detector is then incrementally or continuously orbited about the patient and an ECT study is made.

Alternately the detector is maintained in a stationary position, as is the patient, for a still or so-called spot image. As a still further alternate the detector is maintained in a stationary position while the patient and stretcher are moved into and at least part way into the through hole to conduct what the manufacturer claims to be a whole body study.

The described commercial device has a number of disadvantages. One is that a change of collimators is rather difficult to accomplish. It is necessary to put a prop under the counterweight to support the yoke before removing a collimator and replacing it with another collimator. It is also necessary to be certain that the collimators available for use on the camera all are substantially equal in weight to maintain the counterbalanced condition which is needed to perform the described diagnostic studies.

Another disadvantage of this machine is that the described whole body and ECT studies can only be accomplished on a patient after he has been transferred from his bed to a mobile stretcher and thence to the patient table of the detector system.

In another commercial system, a gantry is provided that has a ring, and defines a patient aperture in its middle. The ring carries one or two U-shaped yokes. The yokes are pivotally mounted on the ring and each carries a nuclear detector at its closed end. At the open end of the U, a pair of spaced counterweights are provided. A stretcher is cantilever supported on a side of the yoke opposite the detectors.

When the latter machine is in use, the patient is positioned on the stretcher and the stretcher is then moved axially through the gantry aperture to position the patient relative to the detector or detectors. With this machine anterior and posterior spot images can be concurrently produced or both detectors may be used for ECT studies. The manufacturer also claims a capability of conducting whole body scans. Again, whole body scans, to the extent they may be achievable, require that a hospitalized patient be moved from his bed to a transporting stretcher and thence the machine stretcher if a whole body study is to be, and can be, conducted.

DISCLOSURE OF THE INVENTION

With a machine in accordance with the present invention, a gantry is provided having an upper support structure defining a through patient aperture is recipocatably mounted on a track by way of a wheeled carriage gantry section. The gantry movably supports a nuclear detector. A pedestal is provided at one end of the track structure to support a patient table or stretcher in cantilevered fashion over a portion of the track structure.

If a study is to be conducted with a patient supported on the cantilevered stretcher, the gantry is moved away from the stretcher to allow free and easy patient access to the stretcher. Once the patient is positioned, the gantry is driven along its reciprocal path of travel to position the detector relative to the patient and permit the conduct of any of spot studies, whole body studies, or ECT studies. With a machine which has been made in accordance with this invention and which has been tested, the range of gantry motion is sufficient to conduct studies which are essentially equivalent to whole body studies of a patient on the cantilevered stretcher.

The machine of this invention is the first machine with capabilities of conducting both ECT studies and whole body studies of even the tallest of patients, and with the patient still in his own bed or stretcher, i.e., without placing him on the machine stretcher. To accomplish this, the upper support section of the gantry is supported on a lower wheeled gantry carriage section. The carriage supports the gantry support section for rotation about a vertical axis. An indexing lock is provided selectively to fix the gantry support section either in a position where the axis of the through patient aperture parallels the path of reciprocal travel or where the axis is perpendicular to the path.

With the gantry positioned with its patient aperture axis perpendicular to the path of gantry travel, a patient may be positioned parallel to the track. The gantry is then driven along its path of travel with the detector positioned relative to the patient such that a whole body study can be conducted. Alternately, the still or spot images can also be obtained with the detector in this position.

ECT studies can also be performed without placing the patient on the machine table or stretcher, by aligning the patient beside the track and perpendicular to it on a cantilevered stretcher. The sidewards-extending detector can then be orbited around the patient for an ECT study.

The preferred indexing lock is a spring biased pin which is carried by one section and projects into a selected one of a plurality of locating holes in the other section. A solenoid is provided to remove the pin from a selected locating hole when it is desired to relatively rotate the gantry sections.

The gantry reciprocal travel is accomplished with a unique drive system. In the preferred and disclosed arrangement, a gantry drive motor is positioned in the stretcher pedestal. Driven and idler chain sprockets are respectively mounted near opposite ends of the track structure for rotation about spaced and vertical axes. The gantry drive motor is drivingly connected to the idler sprocket to rotate that sprocket. A chain is reeved around the sprockets and fixed to the carriage section. Accordingly, rotation of the driven sprocket will cause gantry movement in one direction while reversal of the rotation will pull the gantry in the opposite direction.

The span of chain between the gantry connection and the sprockets is located below an opening in a fixed cover and protective panel. The opening is enclosed by a novel shroud of flexible material which is fixed at its ends to the carriage and reeved over a spaced pair of rollers mounted at opposite ends of the track structure for rotation around horizontal axes.

The gantry includes a novel and improved detector positioning and manipulating mechanism. A spaced pair of weighted support arms are provided. A ring gear is journalled in the upper support section of the gantry for supporting the weighted arms. A square frame structure is fixed within the ring gear and journals the weighted arms on opposite sides of the patient aperture for rotation about axially aligned pivots. A gamma camera detector is pivotally mounted between the weighted arms near the arm ends opposite the weights.

An arm tilt motor is mounted on the square frame and above the portion of the square frame which is normally the top. The arm tilt motor has output shaft portions extending in opposite directions along an axis parallelling the weighted arm pivot axis. These shaft arms are gear drive connected to the weighted arm pivots selectively to cause motor driven weighted arm pivoting, or, through the friction of the system, to maintain the weighted arms in an adjusted position.

A detector tilt motor is mounted to one side of the square frame and chain drive connected to a driven sprocket which is mounted for rotation about an axis parallel to the arm tilt axis. The driven sprocket is chain connected to a detector sprocket mounted coaxial to the detector tilt axis. Accordingly, operation of the detector tilt motor will cause tilting of the detector to bring the face of the detector into an orientation desired for a study. When the detector tilt motor is not operating, a normally on friction brake locks the detector in the attitude to which it has been adjusted by the detector tilt motor.

When the detector tilt motor is not operating and the detector brake is actuated, rotation of the weighted arm motor to raise or lower the detector relative to the patient will not change the detector orientation relative to the patient. Rather, the detector tilt chain will cause the detector to tilt to maintain an orientation of the face of the detector, for example, parallel to the floor, throughout the range of weighted arm tilting movement.

The construction of the gantry provides simplified collimator change. In use, the gantry upper support section is pivoted about a vertical axis to its position in which the detector is alongside, as contrasted with over, the tracks. The weighted arms are then pivoted to place the detector at a convenient height for the collimator change. The tilt drive friction is ample to hold the detector in position as the detector is "unweighted" by removal of one collimator onto a conventional collimator cart. Further, because the tilting is powered, the replacement collimator may be of a different weight than the original.

In the preferred embodiment the tracks or rails which support the gantry are aluminum extrusions each with a flat steel strip secured to the aluminum to provide a wear surface for the gantry's supporting wheels. Each of the rails includes an upstanding flange portion which coacts with the carriage to maintain it in its reciprocal path as it is moved back and forth along the rails.

Brushes are provided to clean the rails of the track and inhibit dirt collection on the wheels and along the track. Such dirt collection, if permitted, might cause excessive wheel and track wear and misalignment of the gantry as it moves along its tracks. Accordingly each wheel is engaged by a brush which is canted with respect to the wheel so that the brush cleans the wheel.

A dual detector version of the mechanism is provided. With the dual detector version, two pairs of weighted arms are mounted for pivotal rotation about spaced and parallel axes. One of the pairs of weighted arms is more closely spaced than the other pair so that the counterweights will nest one pair within the other and provide an enhanced range of detector motion as compared with prior mechanisms.

In the dual detector version, each arm has its own weighted arm tilt drive system and detector tilt system. The detector tilt motors are positioned on opposite sides of the gantry patient aperture while the arm tilt motors are positioned above and below the aperture.

There is also provision for so called rectangular detectors. Rectangular detectors are advantageously used for whole body studies because they can be of sufficient longitudinal dimension to span across the entire patient. This permits a whole body study to be done with an Anger type camera in a single pass rather than two passes along spaced and parallel paths, which is commonly required.

Accordingly, an object of this invention is to provide a novel and improved medical diagnostic imaging system and a method of conducting medical diagnostic studies.

Other objects and a fuller understanding of the invention may be had by referring to the following description and claims, taken in conjunction with the accompanying drawings.

BRIEF DESCRIPTION OF THE DRAWINGS

FIG. 6 is a side elevational view of the alternate embodiment of the system of FIG. 1 shown in FIG. 4;

FIGS. 7 and 8 are detailed views showing alternate embodiments of a portion of the system of FIG. 1;

BEST MODE FOR CARRYING OUT THE INVENTION

Figure 1:
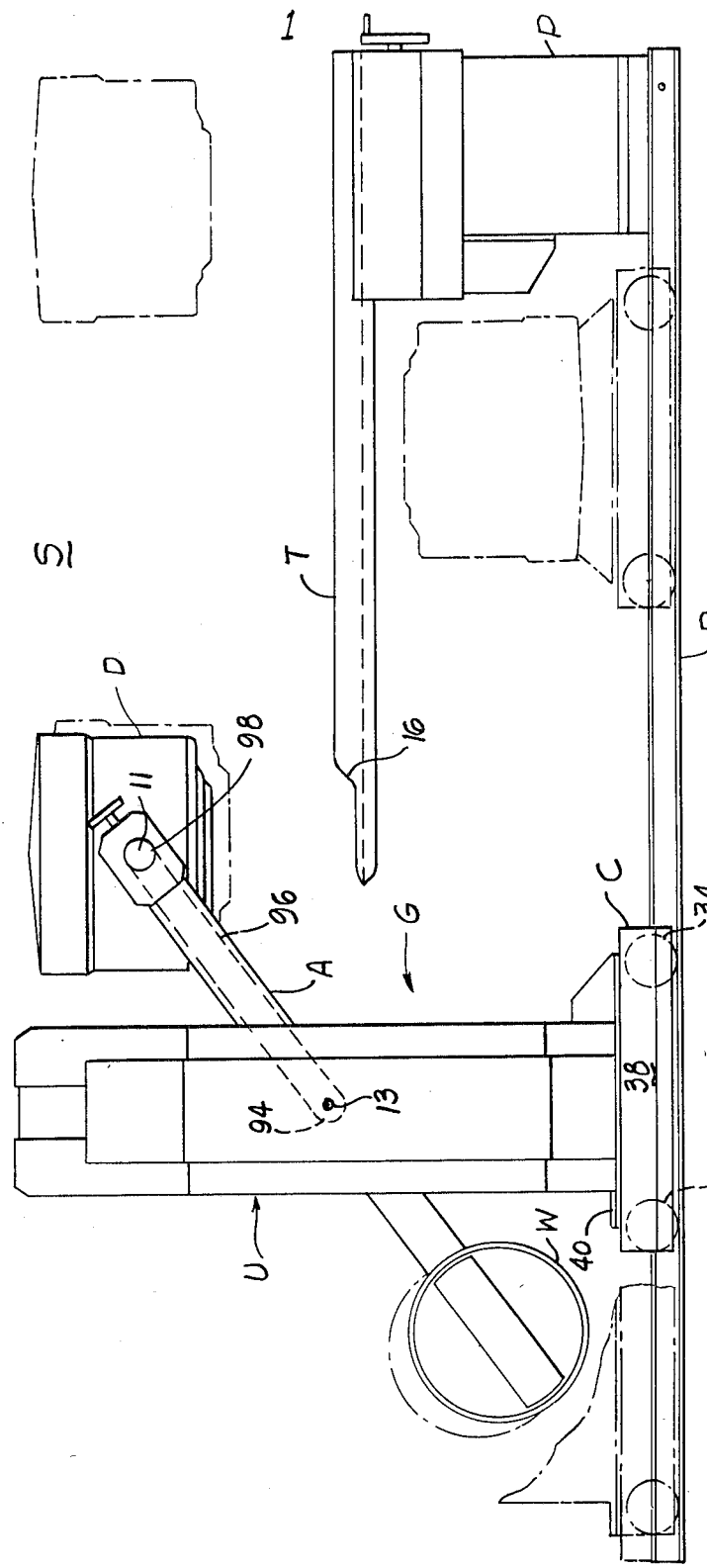
FIG. 1 is a side elevational view, partly in phantom illustrating a system incorporating the present invention.

A nuclear medicine diagnostic system S embodying the present invention is shown in FIG. 1. The system detects nuclear radiation emanating from a patient who has been administered a radiopharmaceutical and produces from the detected radiation an image of internal body structure or condition of the patient, or other diagnostic information.

The system S includes a stationary patient table T supported by a pedestal P, a nuclear detector D supported in a manner described in more detail below. The detector is coupled to known data processing and display equipment to process information from the detector into tangible images of patient body structure or condition or into other forms of diagnostic information.

The system S also includes a gantry G having an upper detector support section U and a lower carriage section C.

The detector mounting section U includes a pair of parallel weighted arms, A (see also FIG. 2), to one end of which the detector D is pivotally mounted for tilting rotation about an axis 11 perpendicular to the parallel arms. The arms are in turn pivotally coupled to the upper support section U gantry for rotation about an axis 13 parallel to that of the detector tilt axis, such that rotation of the arms A adjusts the distance between the detector and the patient. The end of each of the arms A opposite the detector is provided with a counterweight W in order to facilitate implementation of the pivotal motion of the arms.

The upper support section U is vertically mounted on the wheeled trolley or carriage section C. The carriage section C engages a rail system R for limiting movement of the detector support unit U to reciprocal linear movement to the right and left, as shown in FIG. 1.

By manipulating and moving various portions of the upper detector support section, the detector D can be located adjacent nearly any portion of the patient's body, either above or below the patient. In a manner described in more detail below, the detector mounting unit is also provided with means for causing the detector to move in a circular orbit about a patient.

Accordingly, apparatus embodying the present invention is capable of taking "spot" pictures of the patient's body (when the detector is held still), conducting whole body scans of the patient by moving the detector longitudinally with respect to the patient, and for performing emission computed tomography (ECT) by orbiting the detector steps about the patient's body.

The pedestal P is a generally box-shaped structure having a sturdy internal frame and an outer housing defining a hollow space within. The pedestal is firmly fixed with respect to the rail system R and, accordingly, with respect to the floor of the room in which the system S is located.

The patient stretcher or table T is firmly mounted to the top of the pedestal near the table end opposite the detector. The longitudinal dimension of the table is parallel to, and centered over, the rail system R. The table comprises a relatively thin, but strong, elongated portion of carbon fiber material which defines a stepped down portion 16 for comfortably accommodating the patients head.

The firm and stationary mounting of the patient table provides a solid support for the patient to lie upon, and is believed to aid patient comfort. Moreover, the secure and stationary location of the table assists in maintaining a precise and accurate spatial relationship between the patient's body and the detector D.

Figure 5:
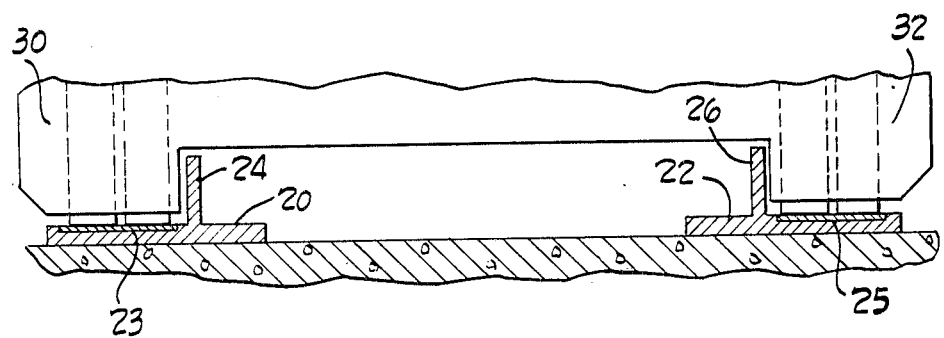
FIG. 5 is a detailed end cross sectional view of a portion of the system of FIG. 1.

The rail system R is shown in cross-section in FIG. 5. The rail system comprises a parallel pair of aluminum rails 20, 22. The rails 20, 22 have upstanding flange portions 24, 26, respectively. The upper surfaces of the rails, outwardly from their respective flanged portions, are provided with steel wear surface inserts 23, 25, for respectively accommodating a wheel, such as 30, 32 of the carriage section C. The smoothness of the rolling surface of the rails is important in order to maintain accuracy of positioning of the gantry. Preferably, the rails 20, 22 are slightly inwardly inclined, in order to facilitate maintenance of the gantry on the path defined by the rail system.

The carriage C of the gantry, which rides upon the rail system, comprises a sturdy, generally rectangular frame 38 on which is mounted a horizontal plate 40 for supporting the upper section of the gantry G. The carriage also comprises two pairs of wheels (only one pair of which, represented by reference characters 31, 34, is shown in FIG. 1) which ride upon the rails 20, 22. The wheeled carriage and the rail system cooperate to facilitate guided linear gantry movement to the right and to the left as shown in FIG. 1.

The detector D comprises a known type of 37 or 61 tube nuclear camera head, such as those manufactured and sold by Picker International, Northford, Connecticut, U.S.A., and known by the trademark "Dyna". In use, a radiation collimator of known design, (not shown) such as of the type having parallel hexagonal holes, is coupled to the face of the detector.

The detector, in response to radiation from the patient, produces and decodes electrical signals in known fashion indicating the location, within the camera field of view, of the impinging radiation. These electrical signals are transmitted by a cable (not shown) to a downstream data processing system which, by known means, processes the incoming data from the detector and utilizes it to generate diagnostic information indicating the configuration and/or condition of internal body organs of the subject patient. Examples of such data processing equipment and techniques is described in the following publication, and the references cited therein, all of which are expressly incorporated by reference:

Buddinger, T. F., et. al, "Emission Computed Axial Tomography", IAEA Symposium on Medical Radionuclide Imaging, Oct. 25-29 1976, Los Angeles, IAEA-SM-210/124.

Figure 12:
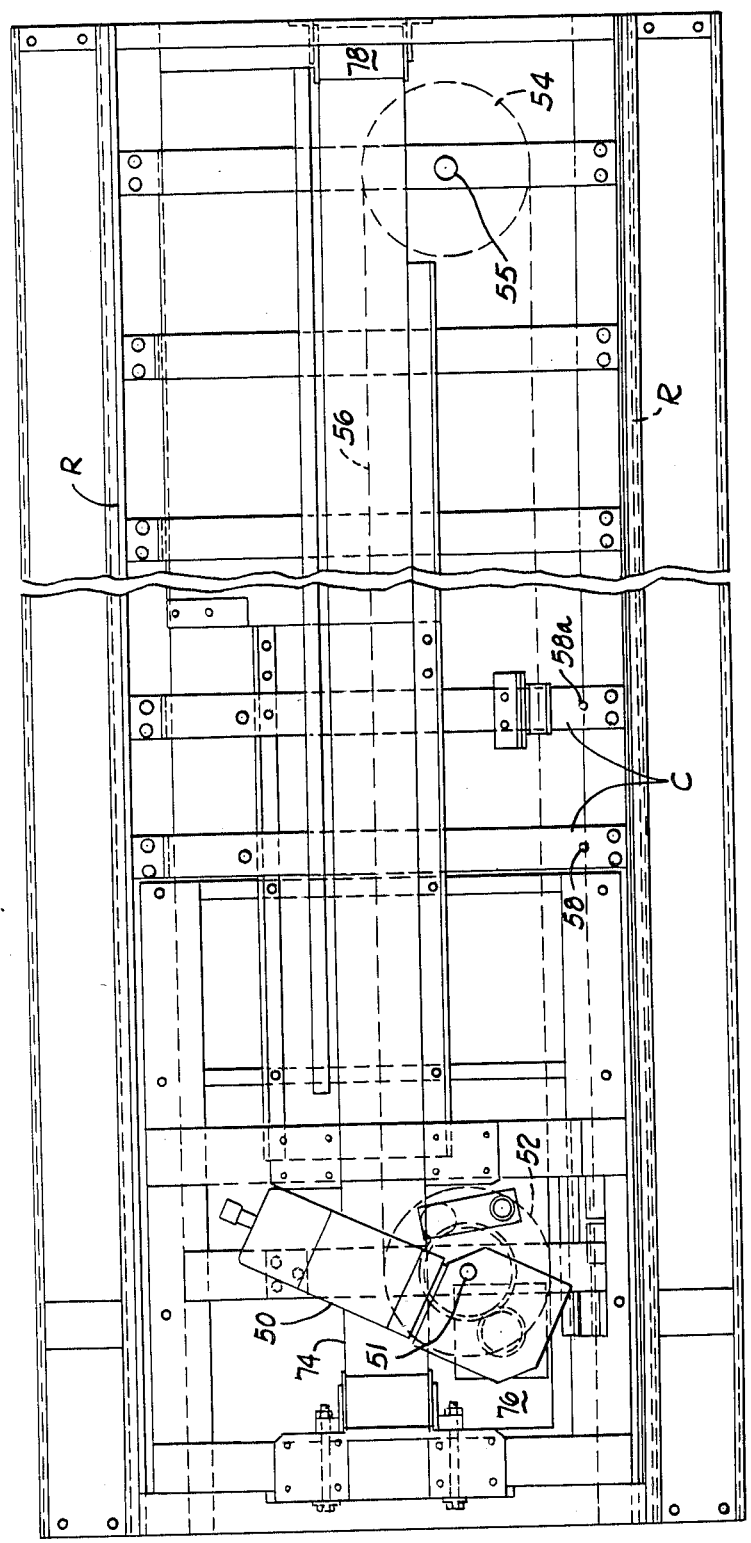
FIG. 12 is a detailed plan view, partly in cross section, of a portion of the system of FIG. 1.
Figure 13:
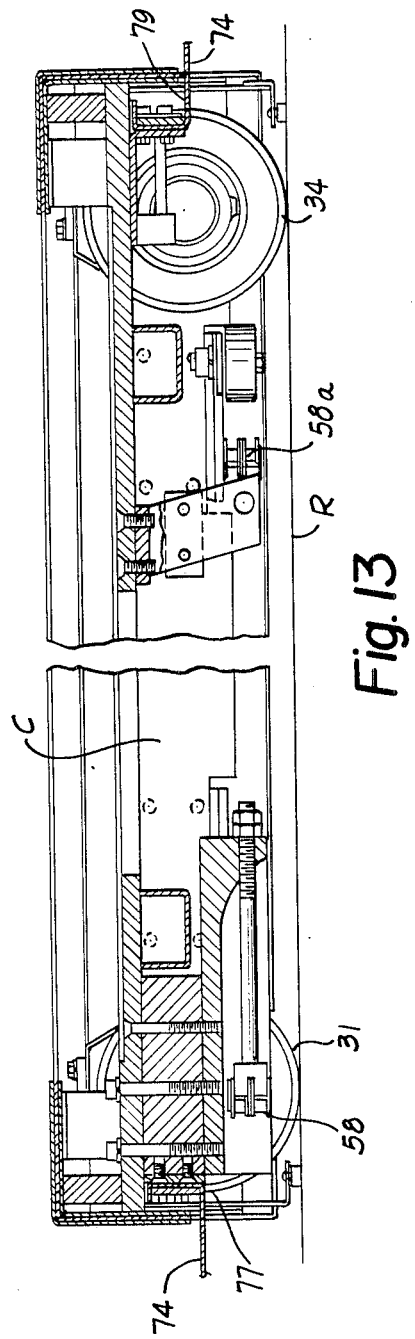
FIG. 13 is a detailed elevational view, partly in cross section, of a portion of the system of FIG. 1.
Figure 15:
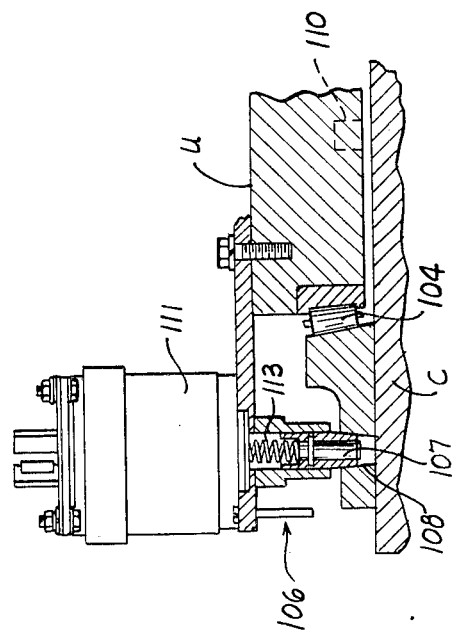
FIG. 15 is a detailed view, partly in cross section and broken away, of a portion of the system of FIG. 1.

Mechanism is provided for power actuating the reciprocal travel of the gantry along the rail system. The gantry power drive includes a motor 50, a pair of drive and idler sprockets 52, 54, respectively, and a connecting chain 56 coupled to the carriage section. Refer to FIGS. 12 and 13.

The motor 50 is located within the pedestal P, and has a vertical output shaft 51 to which is attached the drive sprocket 52. The idler sprocket 54 is located near the opposite end of the rail system and is journalled for free-wheeling rotation about a vertical axis on a shaft 55. The elevation of the driving and idler sprockets 52, 54 relative to the rail system is approximately equal.

A gantry drive chain 56 is reeved about the sprockets 52, 54. The chain 56 is not endless. Rather, the opposite ends of the chain 54 are fixed to the carriage C by way of a chain connect elements 58, 58a.

From the above description, it can be seen that, when the motor 50 is actuated for operation in one direction the gantry is caused to move in a linear path along the rail system in a first direction. When the motor 50 is reversed, the gantry moves in the opposite direction.

In use, prior to the arrival of a patient for examination by the system of this invention, the gantry power drive is actuated to move the gantry to near the limit of its leftward motion, as shown in solid lines in FIG. 1, to a "park" position. With the gantry thus relatively distant, patient access to the table T is essentially unimpeded. Following proper positioning of the patient on the table, the gantry power drive is reversed, and causes the gantry to move the detector to a location laterally adjacent the patient's body.

As described more fully below, the gantry defines a through aperture 60 (FIG. 2) large enough to permit the relative passage therethrough of the patient's body and the table. Since the weighted arms A are parallel, and are not coupled together other than by way of the detector, the arms do not interfere with the relative extension of the patient's body and the table into the aperture.

It can be seen that the range of motion of the detector of this system relative to the patient's body extends over almost the entire height of the patient. Tests have shown that the detector, when located above the table, can be moved over approximately 1.8 meters of the patient's body. With the detector positioned below the table, the corresponding movement is approximately 1.1 meters. Both of these ranges are substantially greater than those available with prior art systems.

Figure 14:
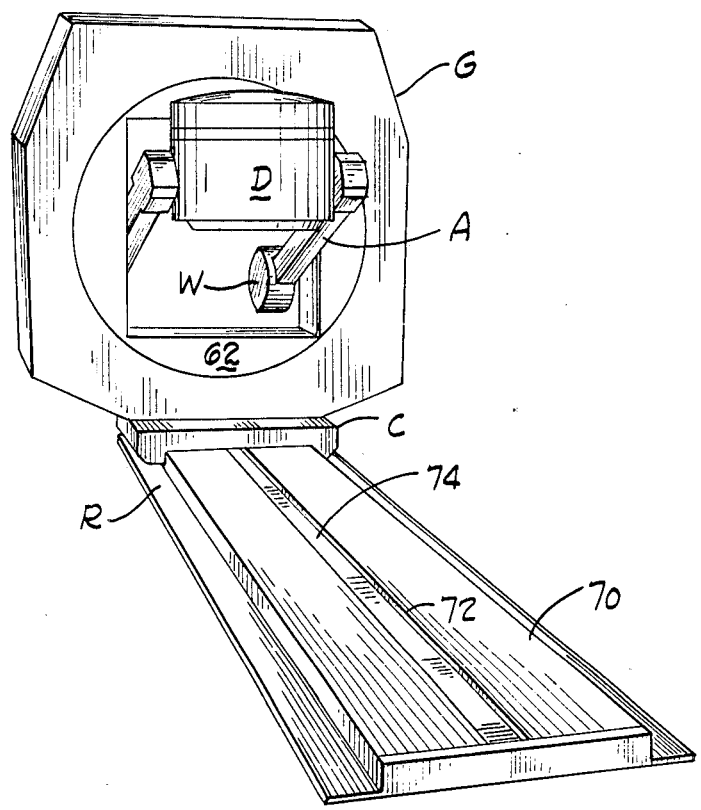
FIG. 14 is a perspective view of a portion of the system of FIG. 1.

The gantry power drive apparatus described above is located between the parallel rails of the rail system R and is enclosed in a cover panel 70 (see FIG. 14). The cover panel 70 defines an elongated opening or slot 72 to permit coupling between the chain connect elements 58, 58a and the carriage section as the gantry proceeds along the linear path described by the rail system.

A novel type of cover apparatus (FIG. 14) is provided to inhibit the entry of dust and other debris into the cover panel 70, where it might adversely affect the gantry power drive apparatus. This cover apparatus includes an elongated cover strap 74, which is made of a suitable flexible and durable material, such as plastic. The cover strap 74 is reeved about a pair of horizontally mounted rollers 76, 78 which are mounted by journalling apparatus on horizontal axes perpendicular to the rail system. Opposite ends of the cover strap are connected to the carriage C, as shown at 77, 79 of FIG. 13. As the gantry moves back and forth in its reciprocal motion along the linear path defined by the rails, the cover strap moves with it, such that the portion of the longitudinal slot 72, other than the portion through which the chain connect elements extend, is constantly covered during operation.

Figure 2:
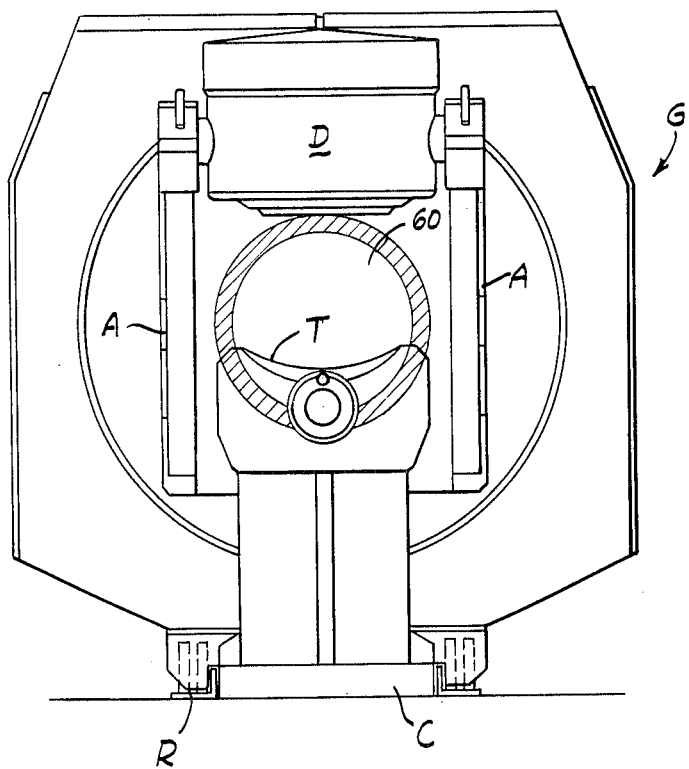
FIG. 2 is an end view of a portion of the system of FIG. 1.
Figure 9:
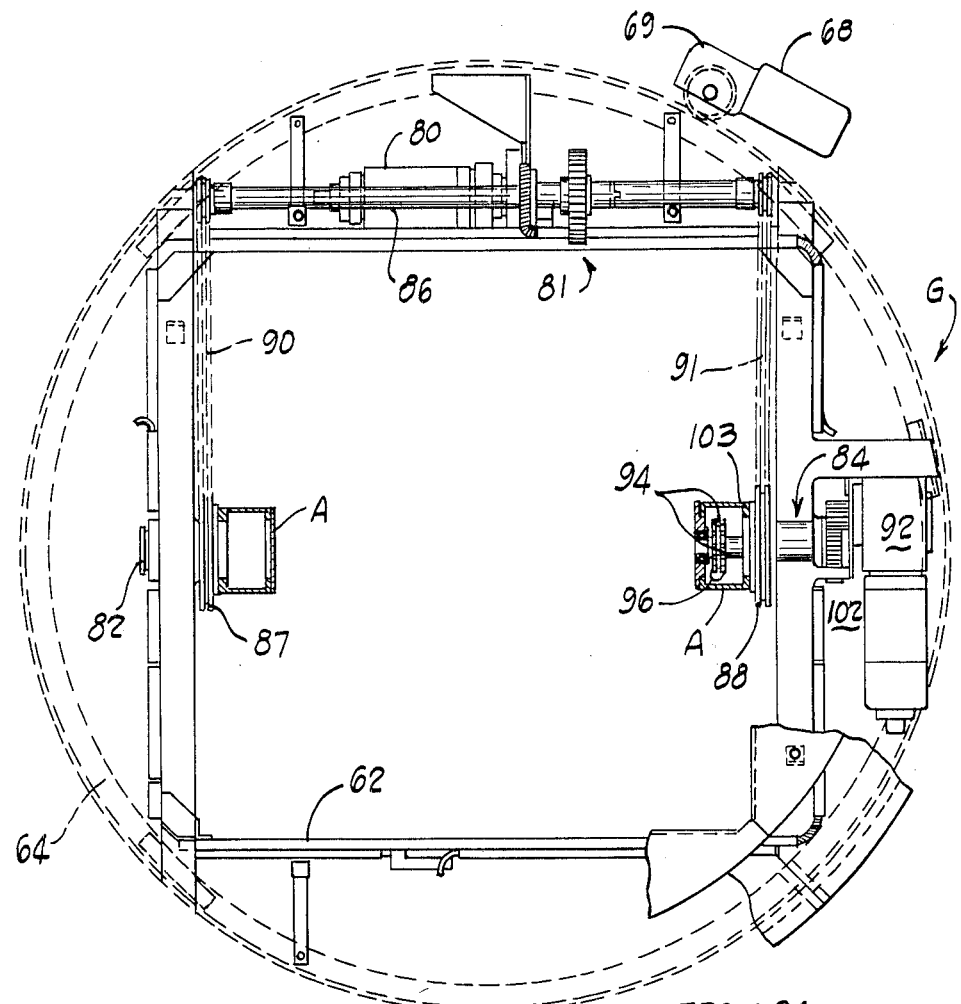
FIG. 9 is a detailed end view showing a portion of the system of FIG. 1.

FIGS. 2 and 9 illustrate the gantry G in greater detail. The gantry defines a patient aperture large enough to permit passage therethrough of a patient aperture on the table. The through hole 60 is defined inside a large upstanding ring gear 64, which is supported as part of an integral bearing in known fashion.

The weighted arms A are respectively journalled at 82, 84, to opposite inside portions of a square frame 62, which is in turn inside and fixed with respect to the ring gear 64.

An orbit motor 68 is drivingly coupled by gearing 69 to the ring gear 64. The orbit motor is mounted fixed with respect to the gantry, and operation of the orbit motor causes rotation of the ring gear 64, and of the square frame assembly 62 fixed within it, about the ring gear axis, which is coaxial with the patient aperture 60. The orbit motor 68 is reversible, such that, by its operation, the detector D, supported on the arms A, is caused to orbitally rotate about the patient's body in either direction of rotation.

This orbital motion can be either continuous or stepwise, depending on the operation of the motor and requirements of the study being performed. It is this orbital motion which enables the conduct of ECT studies with the system of this invention.

Mechanism is provided for power adjusting of the spacing between the detector and the patient's body, relative to the gantry aperture axis. An arm tilt motor 80 (see FIG. 9) is attached to the frame 62. The arm tilt motor has an output shaft 86, which parallels the axis of arm tilt motion. The motor 80 is coupled to drive the shaft 86 by way of gearing 81. The output shaft is connected by double chains 90, 91 to sprockets 87, 88, which are fixed to the respective arms, such that when the arm tilt motor 80 is actuated, the arms are caused to tilt about their pivot axis 13. As in the case of the other motors described above, the arm tilt motor is also reversible, and thus can be used to tilt the arms to move the detector closer to, or farther from, the patient's body, as desired.

The arm tilt power drive mechanism is deliberately constructed to have substantial friction in its linkage. This friction, along with the provision of a very low drive gear ratio, serves to maintain the arms A in their adjusted tilt location when the power arm tilt is deactuated. The friction is sufficient even to hold the arms in their adjusted tilt when the collimator, weighing several hundred pounds, is removed from the detector D. This enables an operator to remove and replace a collimator without need for providing a prop or other means to hold the weighted arms still during the change.

The added friction of the tilt linkage does not inconvenience the operator, because the power tilt drive is sufficiently powerful to easily overcome the friction when power tilting is desired.

Figures 10, 11:
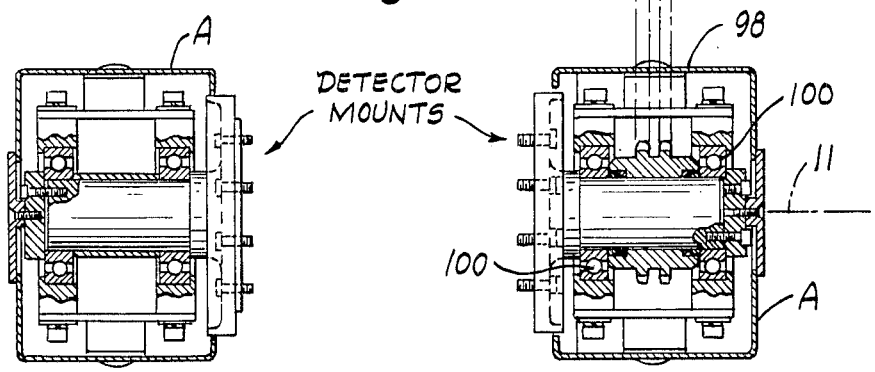
FIGS. 10 and 11 are detail views, partly in cross section, of another portion of the system of FIG. 1.

Detector tilt apparatus is also provided. A detector tilt motor 92 is also mounted on one side of the square frame 62. The detector tilt motor is coupled to drive a sprocket 94 about an axis parallel to the arm tilt axis 11. The sprocket 94 is in turn coupled by a chain 96 to a detector sprocket 98 (see FIG. 11). The detector sprocket 98 is mounted near and housed within the detector end of the arms, for rotation about the detector tilt axis 11, parallel to the arm tilt axis. The sprocket 98 is connected to control, by its position, the tilt attitude of the detector, which is itself pivotally mounted for rotation about the detector tilt axis parallel to the arm tilt axis by way of journalling structure 100.

Accordingly, actuation of the detector tilt motor 92 will cause the detector to tiltingly rotate about its detector tilt axis.

The motor 92, and an associated gear drive connecting it to the sprocket 94 have sufficient internal friction, and a sufficiently low gear drive ratio, to effectively "lock up" the sprocket 94 when the motor 92 is deactuated.

When the motor 92 is deactuated, its friction and inertia prevents rotation of the sprocket 94 with respect to the gantry. This feature provides a particular advantage. When the motor 92 is deactuated, locking up the sprocket 94, the detector is maintained in a constant tilt attitude, with respect to the patient, to which it has been adjusted. More specifically, when the sprocket 94 is held locked, and the arm tilt motor 80 is actuated, causing tilting of the arms A as described above, the detector maintains its previously adjusted tilted attitude with respect to the horizontal. This maintenance of constant detector tilt endures continuously throughout the tilting of the arms. Thus, this feature obviates the need for readjusting detector tilt each time the arms are tilted in order to maintain constant detector attitude with respect to the patient. It also serves to permit, where desirable, variations in arm tilt during a single study, without the necessity for any complex equipment to monitor and correct detector tilt in response to the tilting of the arms.

Accordingly, the locking up of the sprocket 94 converts the detector tilt mechanism, (consisting of the sprockets 94, 98, and the chain 96) in effect, to the equivalent of a parallelogram linkage between the gantry and the detector.

In order to provide a positive lock up of the sprocket 94 when desired, a friction brake 103 is provided, coupled to that sprocket shaft. In use, the brake is normally on, being disengaged only in response to actuation of the motor 92.

The detector support section of the gantry G is rotatably supported upon the carriage section C by journalling structure 104. The journalling structure 104 defines a degree of rotational freedom of the gantry upper section about a vertical axis extending through the center of the carriage section.

Magnetic pin indexing lock structure 106 is provided in the detector support section U of the gantry. The pin lock includes a pin 107 which is engageable with either of two indexing or locating holes 108, 110 in the carriage section.

When the gantry is to be rotated, the magnetic pin 107, normally downwardly biased by a spring 113, is actuated by a solenoid 111 to draw the pin upwardly so that it will not engage in either of the holes 108, 110. If it is desired that the gantry upper section be positioned with its patient aperture axis parallel to the rail system, the upper section is rotated to that position and the magnetic lock deactuated, releasing the pin to fall into positive engagement in the hole 108. This engagement maintains the upper support section at precisely this parallel axial position.

The hole 110 is located such that the pin of the magnetic lock will engage the hole 110 only when the upper support section gantry is rotated to a position wherein its axis is perpendicular to the rail system. If this perpendicular axial relationship is desired, the lock is actuated, withdrawing the pin, and the support section rotated to the desired perpendicular axial position, whereupon the lock is deactuated, releasing the pin to engage in the hole 110. In similar fashion to the case of the parallel axial positioning, the lock's engagement in the hole 110 maintains the perpendicular axial rotational position.

This feature gives rise to the advantage that studies can be conducted on patients while they are lying at a location to one side of the rail system. This means that studies can be conducted without the necessity to remove the patient from his bed or stretcher. This can be a significant advantage in cases where studies must be done on critically ill patients, or patients who for some other reason find movement difficult.

Figure 3:
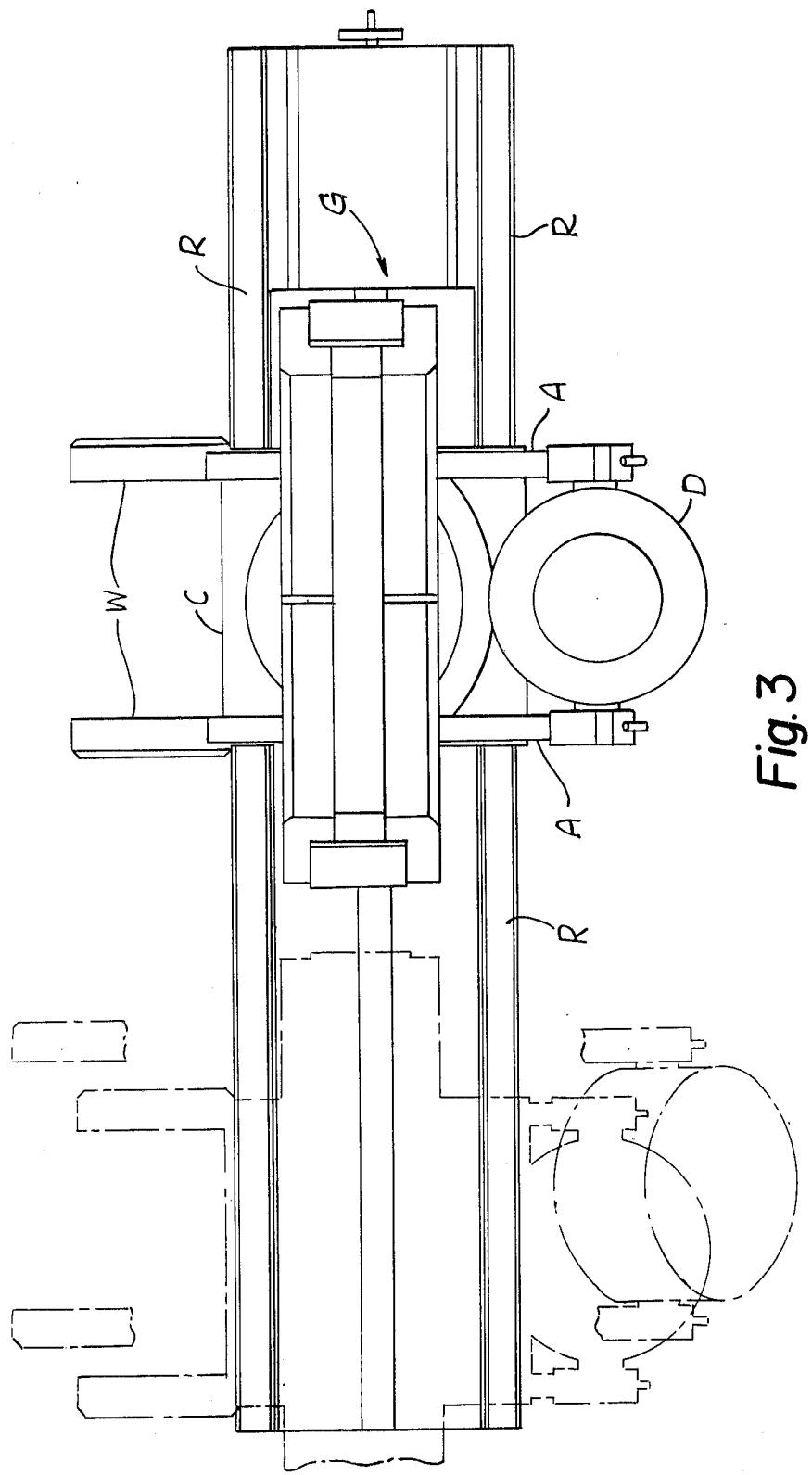
FIG. 3 is a plan view illustrating the system of FIG. 1 in an optional configuration, shown partly in phantom.

ECT, spot and whole body studies can be conducted on patients positioned to one side of the rail system, rather than on the patient table T. In such studies, the gantry detector support section is positioned (FIG. 3) so that its axis is perpendicular to the rail system. The arms and detector can be tilted and orbited freely in the manner described above. For spot imaging, the patient is placed alongside the rails, and the gantry drive mechanism is actuated to position the gantry at the appropriate place along the rail system such that the detector is located adjacent the desired portion of the patient's body.

In conducting whole body studies, the patient is again placed alongside the rail system, the detector and arm tilt are adjusted appropriately, and the gantry power drive system actuated to move the gantry such that the detector passes over the entirety of the patients body. Without interference from the patient table T, and pedestal P, whole body studies can be conducted this way on even the tallest patients.

With the gantry in the perpendicular orientation, even ECT studies can be done, without placing the patient on the table T. To do this, the patient, located on a special cantilevered support, is rolled up alongside and perpendicular to the rails. Arm and detector tilt adjustments are made if required and the detector is then orbited about the patient, by operation of the orbit drive mechanism, in the manner described above.

The preferred embodiment of this invention includes means for inhibiting the accumulation of debris on the rails 20, 22. The presence of such debris between the wheels of the carriage section C and the rails can mar the finish of the mating surfaces of wheel and rail, and result in uneven motion of the gantry as it progresses along the rail system. Such undesirable undulations in motion can result in imprecise detector positioning and motion, which can have an adverse effect on imaging quality.

According to one embodiment, (FIG. 7) a rail cleaner 112 is provided. The rail cleaner 112 includes a plate portion 114 which carries a brush element 116, and can be attached to the carriage by way of screws 118. When so attached, the plate 114 is positioned such that the brush element 116 extends downwardly and impinges upon an associated one of the steel inserts 23, 25. The plate and brush element 116 is located outside the associated wheel, relative to the carriage. In this position, the brush 116 precedes the wheel's progress along the rail such that the rail is swept free of debris ahead of the approaching wheel during carriage and gantry motion.

Another embodiment, as shown in FIG. 8, includes means for brushing carriage wheel surfaces free of debris. In this embodiment, a brush element 120 is mounted by structure 122 to the carriage, in such a way that the brush element 120 impinges against the edge of the wheel. As the wheel rotates, the brush element 120 removes debris from its surface.

Another embodiment of the present invention includes a nuclear imaging system incorporating both an upper detector 128 and a lower detector 130. In use, these detectors are positioned opposite one another with respect to the gantry axis. The upper and lower detectors are mounted respectively to the square inner frame 62 of the gantry upon upper and lower arm pairs 124, 126. The arm pairs 124, 126 are pivotally mounted on the square inner frame of the gantry in a manner similar to that described with respect to the single arm pair A discussed above.

Separate arm tilt and detector tilt drive means are provided in association with each of the upper and lower arm pairs and detectors. The construction of the arm tilt and detector tilt mechanisms analogous to that discussed in connection with the single arm pair A and detector D, and are therefore not discussed in further detail here.

In use, the upper and lower arm pairs 124, 126 can be tilted to maintain a symmetrical positioning of these arm pairs with respect to the gantry axis. In conducting ECT studies, the two arm pairs, and consequently the detectors, are tilted to their desired positions, and the orbit power drive mechanism actuated to cause the two detectors to orbit about the patient's body, one detector being maintained opposite the other. Information produced by the two detectors is then processed in known fashion to derive one or two tomographic images of the patient's body.

Figure 4:
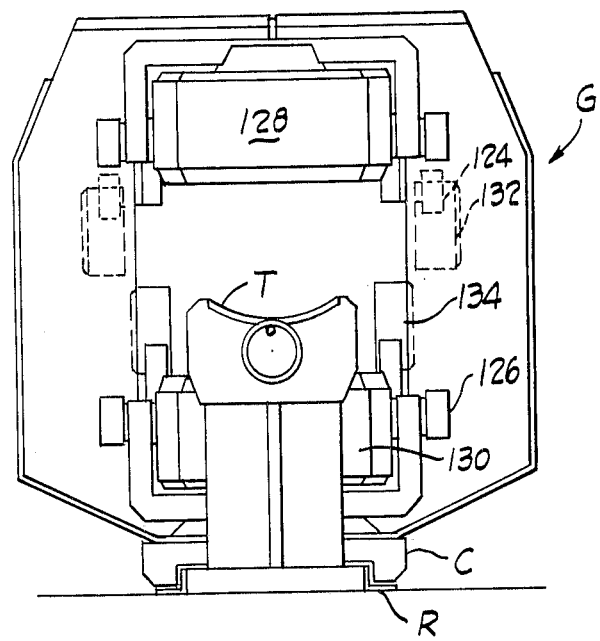
FIG. 4 is an end view of an alternate embodiment of the system of FIG. 1.

Preferably, the arm pairs 124, 126 have differing spacing (see FIG. 4) between their respective members, so that the ends of the arm pairs opposite the detector do not collide when the arm pairs are tilted in a direction to increase the distance between the detectors. Additionally, upper and lower counterweights 132, 134 have differing spacing, which is appropriate for effecting a nesting configuration of the counterweights for preventing collision of the counterweights either with each other or with the opposite arm pair.

This description of the embodiment of the present invention is intended as illustrative, rather than exhaustive of the invention. It is to be recognized that those of ordinary skill in the relevant art may be able to make certain additions, subtractions or modifications in and to this disclosed embodiment, without departing from the spirit or the scope of the invention, as set forth in the appended claims.

We claim:

1. A medical diagnostic mechanism comprising:
   (a) an elongated structure defining a gantry travel path;
   (b) a gantry mounted on said structure for movement along the path of travel;
   (c) drive means connected to the gantry for driving the gantry along its path of travel;
   (d) a nuclear camera detector orbitally mounted on the gantry and positionable spaced from the gantry and proximate a patient for conducting nuclear medical diagnostic studies, and
   (e) means for facilitating rotation of at least a portion of said gantry and of said detector about an axis transverse to said travel path.

2. The mechanism of claim 1 wherein the gantry defines a through patient aperture and a cantilever supported patient structure is provided and positioned to project into the gantry aperture as the gantry is moved through a portion of its path of travel.

3. A medical diagnostic mechanism comprising:
   (a) an elongated gantry supporting track;
   (b) a gantry including a carriage section mounted on the track for reciprocal movement along the track in a path of travel;
   (c) drive means connected to the gantry for driving the gantry along its reciprocal path of travel;
   (d) structure permitting rotation of a gantry section relative to the carriage section about an axis transverse to the path of reciprocation; and,
   (e) a medical imaging device mounted on the rotatable gantry section.

4. The mechanism of claim 3 including structure to index the gantry section into a selected one of a plurality of medical diagnosic study conducting positions.

5. A nuclear diagnostic mechanism comprising:
   (a) a floor support track structure;
   (b) a gantry carriage section movably located on the track for reciprocal movement along a path of travel defined by the track, and an upper detector support gantry section supported by the carriage section and defining a through patient aperture;
   (c) a prime mover operatively coupled to said gantry carriage section, the prime mover including means for moving the gantry along its path of travel;
   (d) the detector support section including a rotatably mounted ring gear and a frame structure connected to the ring gear;
   (e) a pair of spaced, weighted arm structures pivotally supported on the frame structure on opposite sides of the patient aperture for pivotal motion about a common axis generally perpendicular to the axis of the ring gear;
   (f) a nuclear camera detector mounted on the arms for pivotal rotation about an axis paralleling the weighted arm common axis, the moments of said weighted arms and detector about said common axis being approximately zero;
   (g) a detector location drive connected for moving the detector about its detector orientation axis to locate the detector face at a desired orientation relative to a patient position;
   (h) a weighted arm positioning drive connected to the weighted arms for adjustably tilting the arms, and
   (i) said detector location drive including structure for maintaining constant detector alignment at any of a range of detector orientations relative to the patient position during arm positioning drive operation.

6. A nuclear diagnostic mechanism comprising:

(a) a floor support track structure;

(b) a gantry carriage section movably located on the track for reciprocal movement along a path of travel defined by the track, and an upper detector support gantry section supported by the carriage section and defining a through patient aperture;

(c) a prime mover operatively coupled to said gantry carriage section, the prime mover including means for moving the gantry along its path of travel;

(d) the detector support section including a rotatably mounted ring gear and a frame structure connected to the ring gear;

(e) a pair of spaced, weighted arm structures pivotally supported on the frame structure on opposite sides of the patient aperture for pivotal motion about a common axis generally perpendicular to the axis of the ring gear;

(f) a nuclear camera detector mounted on the arms for pivotal rotation about an axis paralleling the weighted arm common axis, the moments of said weighted arms and detector about said common axis being approximately zero;

(g) a detector location drive connected for moving the detector about its detector rotation axis to locate the detector face at a desired orientation relative to a patient position;

(h) a weighted arm positioning drive connected to the weighted arms for adjustably tilting the arms, and (i) an indexing mechanism including means for locating the gantry in a selected one of a plurality of rotatably selectable relative positions.

7. A diagnostic imaging method utilizing a gantry mounted for movement along a predetermined path and an imaging detector coupled to but spaced from the gantry, said method comprising the steps of:

(a) rotating at least a section of the gantry coupled to the detector about an axis transverse to the predetermined path;

(b) placing a patient alongside said predetermined path;

(c) moving the gantry along the path until the detector is operatively located with respect to the patient's body; and, (d) operating the detector to conduct a diagnostic study on the patient.

8. A medical diagnostic method utilizing a detector mounted near one end of an elongated support structure, the support structure being pivotally mounted about a support structure axis, said detector being additionally pivotally mounted with respect to the support structure about a detector axis parallel to the support structure axis, said method corprising the steps of:

(a) positioning a patient proximate the detector;

(b) adjusting tilt of the detector about its detector axis to a predetermined desired detector attitude relative to a patient position and selected from any of a range of said attitudes;

(c) tilting the support structure about its support structure axis; and, (d) maintaining constant said selected attitude of the detector with respect to the patient during support structure tilting motion.

9. An apparatus for use in radiation imaging, said apparatus comprising:

(a) a support structure;

(b) a nuclear imaging detector head;

(c) first mounting apparatus movable coupled to said support structure and coupled to said detector head such that movement of said first mounting apparatus with respect to said support structure changes the tilt orientation of said detector head with respect to a stationary patient position;

(d) drive means for moving said first mounting apparatus with respect to said support structure;

(e) second mounting apparatus coupled between said detector head and said first mounting apparatus for defining a degree of freedom of movement of said detector head with respect to said first mounting apparatus which adjusts said tilt of said detector head;

(f) compensation means coupled to said detector head and responsive to said movement of said first mounting apparatus with respect to said structure to adjust said tilt of said detector head with respect to said first mounting apparatus simultaneously with motion of said first mounting apparatus with respect to said support structure to maintain constant the tilt orientation of said detector head with respect to said patient position.

10. The apparatus of claim 9, further comprising:

(a) tilt adjusting means for adjusting the tilt of said detector head relative to said first mounting apparatus, and (b) said compensation means comprises:

(i) a flexible connecting element;

(ii) coupling apparatus for coupling said flexible connecting element between said detector head and said tilt adjusting means such that said flexible connecting means provides a drive link between the tilt adjusting means and the detector head for effecting detector tilting adjustment, and said flexible connecting element, when said tilt adjusting means is deactivated, acts as a linkage to maintain the detector head orientation in any selected attitude relative to said patient position, over a significant range, during movement of said first mounting apparatus with respect to said support structure.

11. A method of performing a radiation study on a patient utilizing an apparatus including a gantry mounted on a track structure defining a predetermined travel path for the gantry, a detector head attached to and spaced from said gantry, said gantry being rotatable about an axis transverse said travel path, said method comprising the steps of:

(a) positioning the patient alongside, but not over, the track structure;

(b) rotating the gantry about said transverse axis to swing the detector head outwardly transversely displaced from said track structure and generally over the patient;

(c) moving the gantry along the travel path to move the detector head over different portions of the patient's body, and (d) operating the detector head to perform a radiation imaging study.

* * * * *